United States Patent [19]

Van Court Carr et al.

[11] Patent Number: 5,449,832
[45] Date of Patent: Sep. 12, 1995

[54] PROCESS FOR STORAGE AND TRANSPORT OF TOLUENEDIAMINE

[75] Inventors: Richard Van Court Carr, Allentown; Andrew J. Casale, New Tripoli, both of Pa.

[73] Assignee: Air Products and Chemicals, Inc., Allentown, Pa.

[21] Appl. No.: 318,324

[22] Filed: Oct. 5, 1994

[51] Int. Cl.$^6$ .............................................. C07C 209/36
[52] U.S. Cl. ...................................... 564/422; 564/305
[58] Field of Search .................................. 564/422, 305

[56] References Cited

U.S. PATENT DOCUMENTS

| | | | |
|---|---|---|---|
| 4,239,913 | 12/1980 | Veno et al. | 562/425 |
| 4,444,802 | 4/1984 | Winters et al. | 427/27 |
| 4,585,573 | 4/1986 | Yanadori et al. | 252/70 |
| 4,762,946 | 8/1988 | Ritter et al. | 560/179 |
| 4,906,797 | 3/1990 | Lane, Jr. et al. | 585/1 |
| 5,097,903 | 3/1992 | Wilensky | 166/266 |

*Primary Examiner*—Allen J. Robinson
*Assistant Examiner*—Brian M. Burn
*Attorney, Agent, or Firm*—Russell L. Brewer; William F. Marsh

[57] ABSTRACT

This invention relates to an improved process for storing and transporting toluenediamine, particularly for long term storage or storage in large containers, e.g., shipboard containers. The improvement in the process resides in substantially reducing the melting or freezing point of anhydrous toluenediamine obtained by the fractional distillation of a reaction product generated by the hydrogenation of dinitrotoluene. Such melting point reduction is accomplished by adding water in an amount of from 5 to 15% by weight of the toluenediamine and mixing therein for storage and transport. Preferably the level of water introduced to the anhydrous toluenediamine is from about 7 to 10% by weight.

6 Claims, No Drawings

PROCESS FOR STORAGE AND TRANSPORT OF TOLUENEDIAMINE

TECHNICAL FIELD OF THE INVENTION

The invention relates to a process for preparing meta-toluenediamine for storage and transport under liquid phase conditions.

BACKGROUND OF THE INVENTION

Toluenediamine is made commercially by hydrogenating dinitrotoluene manufactured by the mixed acid method. In such process toluene is contacted with nitric acid in the presence of sulfuric acid under conditions for producing a reaction product containing primarily a 2,4- and 2,6-dinitrotoluene isomer mixture (65–80% 2,4- and 20–35% 2,6-). The dinitrotoluene is recovered and then contacted with hydrogen in the presence of a hydrogenation catalyst, e.g., a nickel catalyst. On completion of the hydrogenation, the reaction product containing toluenediamine is distilled under reduced pressure and elevated temperature (360° to 390° F.) and any lights, water, toluidine, orthotoluenediamine and by-products removed. Following distillation, the meta-toluenediamine isomer mixture is recovered from the bottom of the column at a temperature at about 390° F. and passed to a product cooler where the temperature is reduced to about 230°–250° F. and the pressure elevated to atmospheric. The resulting meta-toluenediamine isomer mixture is sent to storage.

Toluenediamine is a high melting aromatic diamine having a melting point of about 105° C. or 220° F. Because of its high melting point, storage and transport becomes difficult, particularly in large containers such as encountered on ships. If the meta-toluenediamine isomer mixture is allowed to convert to a solid, the aromatic diamines may undergo degradation on remelting due to poor heat transfer. Not only is there a problem with stability, there is the problem of remelting a large solid block because of such poor heat transfer. Attempts have been made to granulate toluenediamine for remelting, but such attempts also have remained unacceptable because of poor heat transfer between the solid granules. The toluenediamine isomer mixture then is typically stored in small vessels and transported by truck or transport vehicles equipped to maintain toluenediamine at a temperature in excess of its melting point.

Long term storage and transport in large containers such as present in ocean-going vessels is extremely difficult. One problem association with such storage and/or transport is in the lack of equipment necessary to maintain the stored toluenediamine at a temperature above its melting point. Aside from the equipment requirements for maintaining the toluenediamine at a temperature above its melting point, there is the operational energy cost component associated with the storage and transport process when maintaining the temperature of the toluenediamine above its melting point for an extended period of time.

SUMMARY OF THE INVENTION

This invention relates to an improved process for producing a meta-toluenediamine isomer mixture for storage and transportation, particularly for long term storage or storage in large containers, e.g., shipboard containers. The basic process comprises effecting dinitration of toluene producing a reaction product containing 2,4- and 2,6-dinitrotoluene, hydrogenating the reaction product containing 2,4- and 2,6-dinitrotoluene to 2,4- and 2,6toluenediamine, distilling the hydrogenation reaction product under reduced pressure and elevated temperature producing a final, essentially anhydrous product rich in 2,4- and 2,6-toluenediamine, cooling the final product and transferring for storage or shipment. The improvement in the process resides in substantially reducing the melting point of the anhydrous product rich in 2,4- and 2,6-toluenediamine by adding water in an amount of from 5 to 15% by weight of molten toluenediamine, mixing therein and controlling the temperature of the resultant toluenediamine-water mixture such that the final temperature of the toluenediamine-water mixture is at or below the boiling point. The final product is ready for storage and transport. Preferably the level of water introduced to the anhydrous toluenediamine is from about 7 to 10% by weight.

There are significant advantages associated with the process of this invention and they include:

- an ability to substantially reduce the freezing point of meta-toluenediamines by the addition of a small amount of water vis-à-vis the meta-toluenediamines to permit storage and transport, particularly transport on ocean-going vessels;
- an ability to reduce energy costs associated with maintaining toluenediamine in liquid phase conditions for long term storage or extended transport;
- an ability to convert anhydrous meta-toluenediamines to lower melting meta-toluenediamines suited in conventional equipment;
- an ability to convert meta-toluenediamines to low melting solids without effecting discoloration, substantial byproduct formation and stability during storage; and,
- an ability to remove water from meta-toluenediamines at low temperatures thus saving energy costs associated with high temperature distillation.

DETAILED DESCRIPTION OF THE INVENTION

Toluenediamines are typically produced by the hydrogenation of dinitrotoluene, dinitrotoluene being produced by the mixed acid nitration of toluene. The reaction product obtained from the hydrogenation of dinitrotoluene is fractionally distilled, under vacuum, removing light (highly volatile) material such as deaminated product, ammonia and residual water which is produced during the reaction. Distillation removes the byproducts and residual water from the reaction product thereby generating anhydrous meta-toluenediamines, primarily 2,4- and 2,6-toluenediamine having minimal contaminants therein. The temperature of the meta-toluenediamine isomer mixture recovered from the bottom of the distillation, n column is generally from about 380° to 400° F.

It has been found that one can render the meta-toluenediamines suitable for long term storage and suitable for ship transport without adversely affecting the product during such storage, and transport by reducing the melting point of the meta-toluenediamines from about 200° to 250° F. Melting point reduction is accomplished by adding hot demineralized water, a deionized water or distilled water under pressure to the 200°–250° F. meta-toluenediamines. Water, being soluble in the toluenediamine, mixes readily reducing the freezing point of the mixture to a temperature of about 145° to 165° F. One of the significant advantages of this process is that the water, if introduced hot, (160°-190° F.) only reduces the temperature of the meta-toluenediamine mixture from 220° to 250° F. to about 210° to 235° F. If the water is at 80°-90° F. the temperature is reduced to about 200°-225° F. In either case, the resultant final temperature level provides sufficient internal heat for an extended period of time and an external heat source may not be required. The main point is that the final temperature of the meta-toluene isomer mixture should be below the bubble point, i.e., the temperature at which boiling begins. For a toluenediamine mixture containing about 5% water that temperature is about 256° while a toluenediamine mixture containing about 10% water, that temperature falls to below about; 242° F. Nonetheless, the final temperature is well above the freezing point of the meta-toluenediamine mixture, thus affording substantial residual heat for maintaining liquid phase conditions for extended periods of time.

Water concentrations greater than about 15% can be utilized to reduce the toluenediamine freezing point to a lower temperature, although such reduction in freezing point generally is small and does not result in energy efficiency. Water, because of its high heat capacity not only reduces the temperature of the toluenediamine, energy costs associated with the subsequent removal of the water through distillation are increased.

EXAMPLE 1

Freezing Point Measurements

A series of tests were carried out for the purpose of determining the influence of water on the freezing point and stability of anhydrous toluenediamine in the presence of water. As determined herein, the freezing point is the temperature at which crystallization begins and does not refer to the temperature at which the entire mass of toluenediamine is a solid.

Molten toluene was mixed with various levels of water and cooled at a slow rate. Temperatures were taken of the mass as a function of time. When the temperature held constant for a period of about 15 minutes, the freezing point was noted. The table sets forth the results.

| Freezing Point Temperature °F. | 170 | 165 | 160 | 150 |
|---|---|---|---|---|
| Weight % Water | 3.4 | 4.9 | 5.6 | 10.1 |

The toluenediamine-solute mixtures were found to be stable for a period of 30 days at 185° F. and without phase separation

What is claimed is:

1. An improved process for preparing meta-toluenediamines for storage and/or transportation in large containers, the improvement which comprises:
    adding a demineralized water in an amount of from 5 to 15% by weight to a substantially anhydrous meta-toluenediamine isomer mixture obtained by the fractional distillation of a reaction product generated by the hydrogenation of dinitrotoluene at a temperature of at least 200° F. and mixing the water therein for substantially reducing the freezing point of said substantially anhydrous meta-toluenediamine isomer mixture, and adjusting the final temperature such that the product is at a temperature below the bubble point.

2. The process of claim 1 wherein the water is added at a level of from about 7 to 10% by weight.

3. The process of claim 2 wherein the substantially anhydrous meta-toluenediamine isomer mixture is at a temperature of from 220° to 250° F. when the water is added thereto.

4. The process of claim 3 wherein the water is at a temperature of from 80° to 190° F. when added to the substantially anhydrous meta-toluenediamine isomer mixture.

5. The process of claim 4 wherein the meta-toluenediamine mixture comprises from about 65-80% 2,4-toluenediamine and from about 20-35% 2,6-toluenediamine.

6. In a process for producing a meta-toluenediamine mixture wherein toluene is contacted with nitric acid in the presence of sulfuric acid under conditions for producing a reaction product containing primarily a 2,4- and 2,6-dinitrotoluene isomer mixture, the dinitrotoluene recovered and then contacted with hydrogen in the presence of a hydrogenation catalyst, the resulting reaction product containing 2,4- and 2,6-toluenediamine distilled in a column under reduced pressure and elevated temperature to remove any lights, water, toluidine, ortho-toluenediamine and byproducts, the substantially anhydrous meta-toluenediamine isomer mixture recovered from the bottom of the column and passed to a product cooler where the temperature is reduced to about 200°-250° F. and the pressure elevated to at least atmospheric, the improvement for preparing the resulting meta-toluenediamine isomer mixture for storage and/or transport which comprises:
    adding a deionized water in an amount of from 5 to 15% by weight to said substantially anhydrous meta-toluenediamine isomer mixture at a temperature of at least 220° F.,
    mixing the water with said substantially anhydrous meta-toluenediamine isomer mixture; and,
    adjusting the final temperature such that the product is at a temperature below the bubble point.

* * * * *